United States Patent [19]

Matsumoto et al.

[11] Patent Number: 4,757,003

[45] Date of Patent: Jul. 12, 1988

[54] METHOD FOR THE DETECTION OF CANCER

[75] Inventors: Makoto Matsumoto; Takao Taki, both of Shizuoka; Kenji Arai, Hamamatsu; Hidemi Ishikawa, Shizuoka; Kunio Kurata, Matsudo; Kiyoshi Sekiguchi, Kashiwa; Akio Myoga, Yokohama; Kimimichi Obata, Kashiwa; all of Japan

[73] Assignee: Dainabot Co., Ltd., Japan

[21] Appl. No.: 861,086

[22] Filed: May 8, 1986

Related U.S. Application Data

[63] Continuation of Ser. No. 587,305, Mar. 7, 1984, abandoned.

[30] Foreign Application Priority Data

Sep. 9, 1983 [JP] Japan ................................ 58-165223

[51] Int. Cl.$^4$ .................. G01N 33/53; G01N 33/543; C07H 1/00
[52] U.S. Cl. ........................................ 435/7; 436/518; 436/537; 436/541; 436/813; 436/815; 436/822; 536/1.1; 536/53
[58] Field of Search ............... 536/1.1, 53; 435/7; 436/537, 541, 518, 813, 815, 822

[56] References Cited

PUBLICATIONS

Kannagi et al, Cancer Res., 43(1983), 4997-5005.
Hattori et al, Biochim. Biophys. Acta, 666(1981), 361-9.
Yasuda et al, J. Immunol. Methods, 44(1981), 153-8.
Uemura et al, J. Immunol. Methods, 53(1982), 221-32.
Taki et al, Chem. Abstracts, 97(1982), #4370w.
Abstracts of Japanese JP 58-129363: Patent Abstracts of Japan, vol. 7(1983), #241; Chemical Abstracts, 100(1984), #3090y; Derwent On-Line Abstract; WPIL Database.

*Primary Examiner*—Christine M. Nucker
*Attorney, Agent, or Firm*—Scully, Scott, Murphy & Presser

[57] ABSTRACT

A process for the detection of cancer comprises an immunological assay of a glycolipid present in blood, thoracic cavity fluid, abdominal dropsy or urine wherein the glycolipid can be any one selected from the group consisting of:
(1) asialo $GM_1$: galactosyl-N-acetylgalactosaminyl-galactosyl-glucosyl-ceramide;
(2) asialo $GM_2$: N-acetylgalactosaminyl-galactosyl-glucosyl-ceramide;
(3) fuco $GA_1$: fucosyl-galactosyl-N-acetylgalactosaminyl-galactosyl-glucosyl-ceramide; and
(4) paragloboside: galactosyl-N-acetylglucosaminyl-galactosyl-glucosyl-ceramide.

These glycolipids have been found to increase in body fluids with a proliferation of cancer cells.

13 Claims, 7 Drawing Sheets

METHOD FOR THE DETECTION OF CANCER

This is a continuation of copending application Ser. No. 587,305, filed on Mar. 7, 1984, abandoned.

BACKGROUND OF THE INVENTION

This invention relates to a process for immunologically assaying glycolipid in an organism. Recently there has been observed in many countries a very high mortality rate due to cancer. The expectation, need of detection, and treatment for cancer in its early stage have become progressively greater. Morphological tests such as imaging diagnostic technology and immuno-biochemical diagnostic technology, which is a noninvasive test carried out by collecting a small amount of humors, have been used to detect cancer in its early stage. The role of the immunobiochemical diagnostic technology has become increasingly important. The following have been attempted to detect tumor associated antigens, the number of which would be remarkably increased by the proliferation of cancer cells; to diagnose cancer immuno-biochemically, which has resulted in the finding of α-fetoprotein, carcinoembryonic antigen and the like; and the development of assay systems thereof which are clinically useful in practice. However, these markers are not satisfactory from the viewpoint of an early diagnosis of cancer. Therefore it has been eagerly desired to find a novel tumer associated antigen as well as to develop an assay system and find clinical application thereof.

Turning attention to glycolipid which is one of the constituents of cell membrane, we have investigated the relationship between glycolipid and cell adhesion by analyzing glycolipid in cancerous cells and examining the metabolism thereof. Consequently we have found that the difference in cell adhesion might be represented by the difference in glycolipid metabolism. In particular, a biosynthetic pathway of glycolipid via another glycolipid which is seldom observed in a normal cell has been found in a highly malignant cancerous cell devoid of cell adhesion. That is to say, four different glycolipids have been found to increase with the proliferation of cancer cells. These glycolipids have been identified as asialo $GM_1$, asialo $GM_2$, fuco $GA_1$ and paragloboside as a result of various analyses. The structures of these glycolipids are as follows:

asialo $GM_1$, Gal-GalNAc-Gal-Glc-Cer;
asialo $GM_2$, GalNAc-Gal-Glc-Cer;
fuco $GA_1$, and
paragloboside, Gal-GlcNAc-Gal-Glc-Cer
wherein Gal represents galactose, Glc represents glucose, Fuc represent fucose, GalNAc represents N-acetylgalactosamine, GlcNAc represents N-acetylglucosamine and Cer represents ceramide.

We have found that these glycolipids may be available as novel cancer markers, since they would increase in human cancerous cells and would therefore be extremely useful in cancer diagnosis by determining their concentrations in humors. We have further established a simple process for immunologically assaying these glycolipids with high sensitivity and accuracy. It has been hitherto impossible to clinically determine such a low concentration of these glycolipids in humors.

SUMMARY OF THE INVENTION

An object of the present invention is to provide novel cancer markers.

Another object of the present invention is to provide a process for immunologically assaying glycolipid in an organism.

Other objects and advantages of the present invention will be apparent from the following description.

According to the present invention, glycolipids in an organism, such as asialo $GM_1$, asialo $GM_2$, fuco $GA_1$ and paragloboside, are immunologically assayed by using respective antibodies specific thereto.

Methods of immunological assaying include a method based on a competitive reaction using a labelled antigen, a sandwich method using a labelled antibody and an immunometric assay using a labelled antibody.

Antibodies available for assaying asialo $GM_1$, asialo $GM_2$, fuco $GA_1$ and paragloboside may be prepared by intracutaneously injecting a mixture of one of these glycolipids and a foreign high-molecular carrier such as bovine serum albumin, methylated bovine serum albumin or erythrocytic membrane protein as an antigen into an animal other than a human, such as a rabbit. According to the present invention, asialo $GM_1$, asialo $GM_2$, fuco $GA_1$ and paragloboside in humors can be assayed by an immunological method using an antibody obtained as described above. Alternatively, it is possible to use a monoclonal antibody to assay the glycolipid.

DESCRIPTION OF THE PREFERRED EMBODIMENTS

The present invention will be illustrated more particularly, using asialo $GM_1$ as an example.

1. Assay of asialo $GM_1$ by a competitive reaction:

Asialo $GM_1$ to be assayed and a given amount of labelled asialo $GM_1$ are allowed to competitively react with a given amount of antibody. Then the labelled asialo $GM_1$ conjugated with the antibody is separated from the labelled asialo $GM_1$ not conjugated with the antibody. The activity of the labelling agent in one or both of these fractions is determined to assay the asialo $GM_1$. Alternately, it is possible in such an assay based on the competitive reaction to use a labelled oligosaccharide prepared by labelling the saccharide chain portion (oligosaccharide) of asialo $GM_1$, instead of using the labelled asialo $GM_1$ as the labelled antigen to assay asialo $GM_1$, and allowing the labelled oligosaccharide to competitively react in the same manner as described above.

2. Assay of asialo $GM_1$ by a sandwich method:

Asialo $GM_1$ to be assayed is allowed to react with an insolubilized antibody prepared by conjugating an antibody with an insoluble material (solid phase) to form an antibody/asialo $GM_1$ conjugate. The resulting conjugate is allowed to react with a labelled antibody prepared by labelling an antibody with a labelling agent to form a sandwich-like antigen/antibody conjugate, i.e. antibody/asialo $GM_1$/labelled antibody. Then the activity of the labelling agent on the obtained antigen/antibody conjugate is determined to assay the asialo $GM_1$.

3. Assay of asialo $GM_1$ by an immunometric method:

(1) Asialo $GM_1$ in humors to be assayed is allowed to react with a given amount of a labelled antibody prepared by labelling an antibody with a labelling agent. Then unreacted labelled antibody is adsorbed by an immunoadsorbent prepared by conjugating asialo $GM_1$ with an insoluble material (solid phase). The activity of the labelling agent on the immunoadsorbent is determined to assay the asialo $GM_1$.

(2) Asialo $GM_1$ to be assayed is allowed to react with a given amount of an antibody. Unreacted antibody is adsorbed by an immunoadsorbent prepared by conjugating asialo $GM_1$ with an insoluble material (solid phase). Then, labelled anti-IgG antibody prepared by labelling an anti-IgG antibody against the antibody with a labelling agent is allowed to react with the antibody on the immunoadsorbent. Then the activity of the labelling agent of the labelled anti-IgG antibody conjugated with the immunoadsorbent is determined to assay the asialo $GM_1$.

In these assay methods, a standard curve which has been previously drawn by carrying out the same procedure as described above by using standard asialo $GM_1$ of known concentration is used to determine the amount of asialo $GM_1$.

Table 1 shows the results of a recovery test by the present process. These recoveries were obtained by adding asialo $GM_1$ of various known concentrations to three specimens. The recoveries ranged from 82 to 116%, indicating good results.

TABLE 1

| | Recovery test | | | | | | | | |
|---|---|---|---|---|---|---|---|---|---|
| | Specimen 1 | | | Specimen 2 | | | Specimen 3 | | |
| Added asialo $GM_1$ (ng/ml) | Asialo $GM_1$ concentration (ng/ml) | Recovered (ng/ml) | Recovery (%) | Asialo $GM_1$ concentration (ng/ml) | Recovered (ng/ml) | Recovery (%) | Asialo $GM_1$ concentration (ng/ml) | Recovered (ng/ml) | Recovery (%) |
| 0 | 15 | 0 | — | 15 | 0 | — | 17 | 0 | — |
| 16 | 29 | 14 | 88 | 30 | 15 | 94 | 31 | 14 | 88 |
| 31 | 49 | 34 | 110 | 44 | 29 | 94 | 45 | 28 | 90 |
| 63 | 75 | 60 | 95 | 70 | 55 | 87 | 90 | 73 | 116 |
| 125 | 117 | 102 | 82 | 131 | 116 | 93 | 132 | 115 | 92 |
| 250 | 255 | 240 | 96 | 253 | 238 | 95 | 259 | 242 | 97 |

Figure 7:
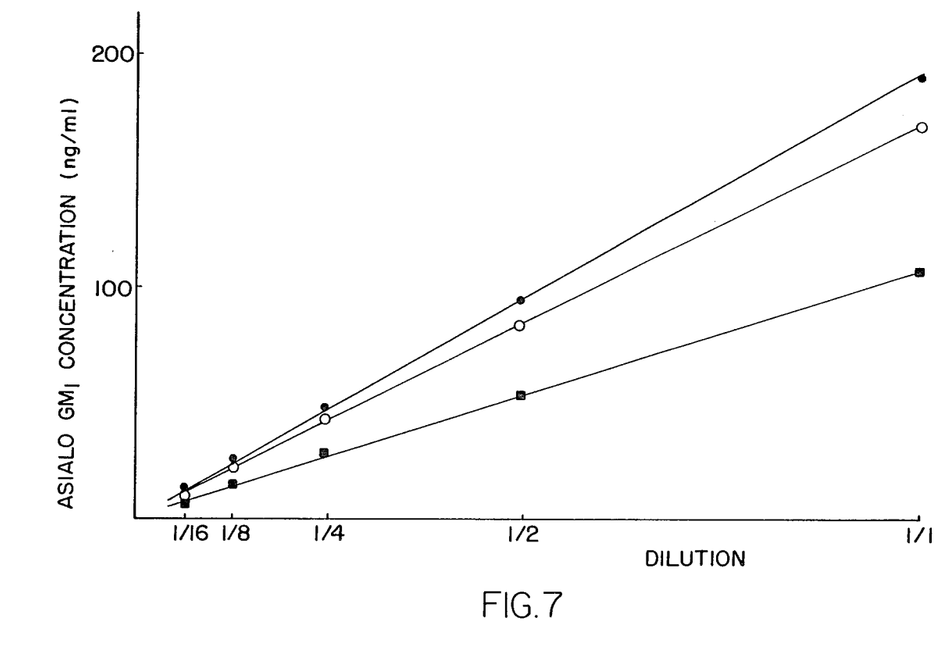
FIG. 7 shows results of a test in which three specimens were assayed by the process of the present invention, with a dilution varied as indicated in the figure.

FIG. 7 shows the results of a dilution test by the present process. The dilution curves are linear, which indicates good results. The results of the recovery and the dilution tests suggest that the present process would be useful in assaying asialo $GM_1$ accurately.

Asialo $GM_2$, fuco $GA_1$ and paragloboside may likewise be assayed by the aforementioned methods of (1), (2) and (3).

Various humors such as blood, fluid in the thoracic cavity, abdominal dropsy or urine may be used in the present process.

Labelling agents such as radioactive materials, enzymes or fluorescent materials may be used in the present invention.

An insolubilized glycolipid, i.e., immunoadsorbent, in which asialo $GM_1$, asialo $GM_2$, fuco $GA_1$ or paragloboside is conjugated with an insoluble material (solid phase), is prepared by chemically conjugating one of these glycolipids with a solid phase or physically adsorbing the former by the latter. An insolubilized antibody in which an antibody against each glycolipid is conjugated with an insoluble material (solid phase), is prepared by the same way. Conventional solid phase such as cellulose, sepharose, glass or polystyrene may be used.

Thus, the present invention has made it possible to assay glycolipid in a trace amount in humors of patients afflicted with various diseases, including cancer, by taking advantage of an antigen/antibody reaction.

Figure 4:
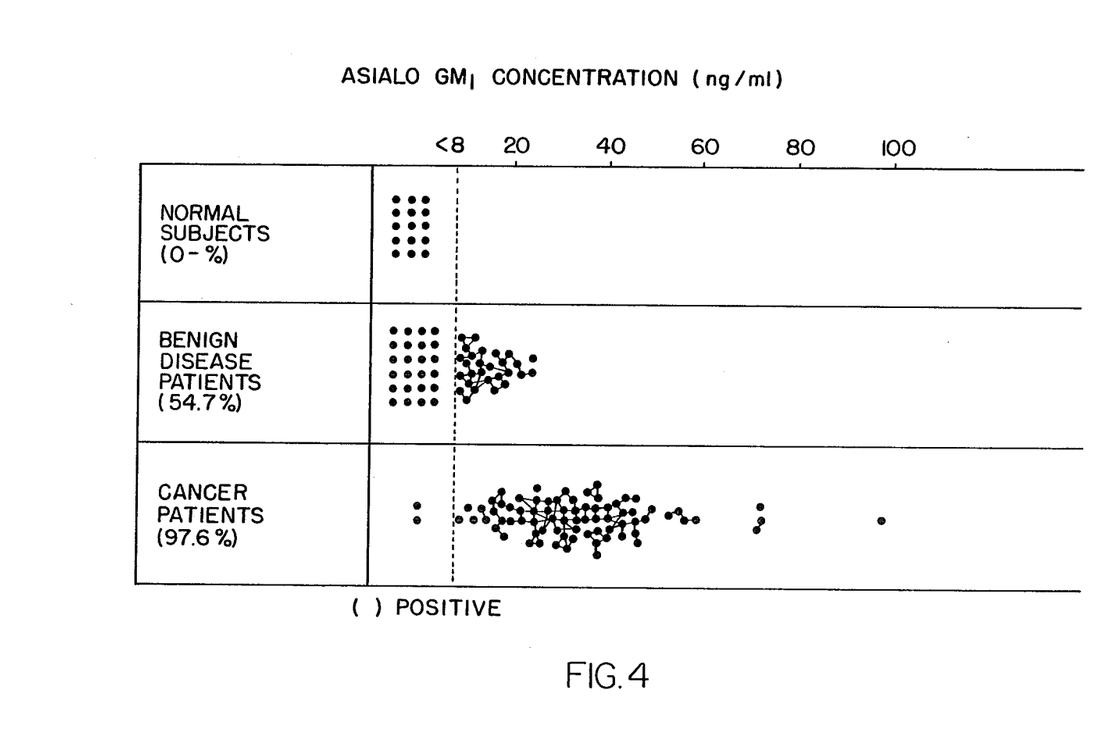
FIG. 4 shows plots of the asialo $GM_1$ concentration in serum of cancer patients assayed by the process of the present invention by comparison with those of benign disease patients and normal subjects. In this figure, the abscissa refers to the asialo $GM_1$ concentration (ng/ml).
Figure 5:
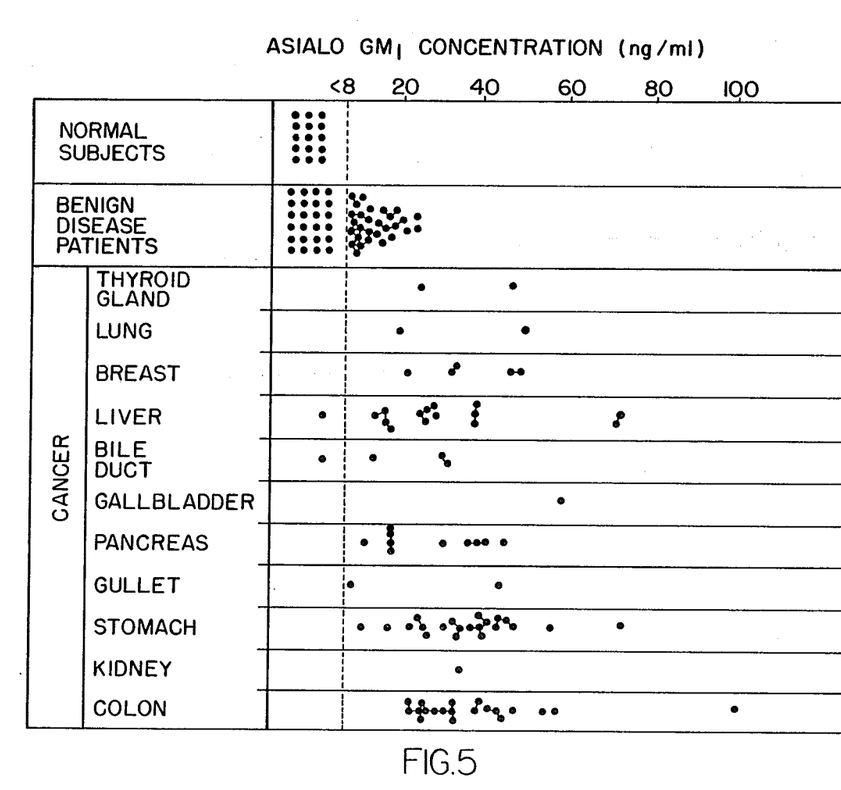
FIG. 5 shows plots of the asialo $GM_1$ concentration in serum of cancer patients that have been assayed by the process of the present invention and classified by the sites of cancer, i.e., thyroid gland, lung, breast, liver, bile duct, gallbladder, pancreas, gullet, stomach, kidney and colon.
Figure 6:
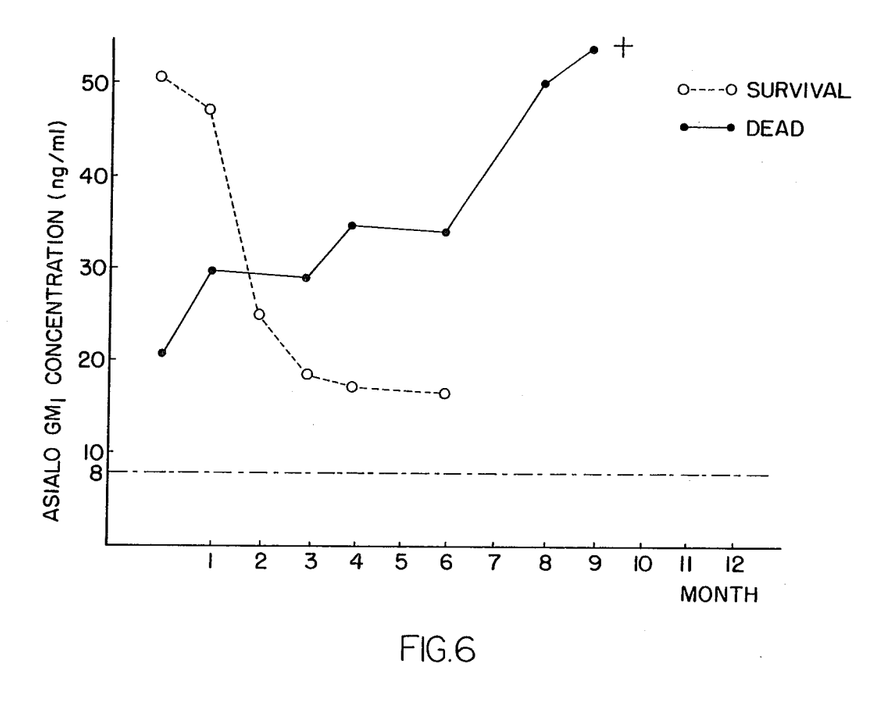
FIG. 6 shows changes in the asialo $GM_1$ concentration in serum of lung cancer patients (survival and dead) with the passage of time during a chemical treatment.

The present process for assaying asialo $GM_1$, asialo $GM_2$, fuco $GA_1$ or paragloboside exhibits excellent reproducibility, high sensitivity and accuracy with simple procedures. Therefore, it is remarkably useful as a daily clinical test method. As shown in FIGS. 4, 5 and 6, using asialo $GM_1$ as an example, assay of these glycolipids in humors by the process of the present invention is extremely effective in the detecting of cancer in its early stage and the examination of the progress of treatment.

EXAMPLES

To further illustrate the present invention, and not by way of limitation, the following examples will be given.

Example

I. Preparation of antigen and antibody

1. Preparation of antigen (glycolipid)
   (1) Purification of asialo $GM_1$
   2.0 g of a glycolipid fraction of bovine brain was hydrolyzed in the presence of 1N formic acid for 1 hour at 100° C. After the completion of the hydrolysis, an asialo glycolipid fraction was separated by DEAE-Sephadex A-25 column chromatography. Sephadex is a type of cross-linked dextrangel; DEAF-Sephadex is a sephadex one anion exchanger. The crude asialo glycolipid thus obtained was further purified by column chromatography with Iatrobeads which are made up of a type of silica gel particle (a product of Iatron Co., Ltd.) in a solvent gradient of $CHCl_3/CH_3OH/H_2O$ of 80:20:0.5 and $CHCl_3/CH_3OH/H_2O$ of 50:45:3.5.

Thus approximately 600 mg of purified asialo $GM_1$ was obtained from 2.0 g of the bovine brain glycolipid.

(2) Purification of asialo $GM_2$ 500 mg of the bovine brain $GM_1$ was dissolved in an acetate buffer solution (pH 4.5). 200 mg of sodium periodate was added and the mixture was allowed to stand in the dark for 10 hours at 4° C. Then a few drops of ethylene glycol was added and the mixture was dialyzed overnight. After adjusting the pH to 8.0 with a borate buffer solution and adding 380 mg of $NaBH_4$, the mixture was allowed to stand for 12 hours at 0° C. Acetic acid was added to cease the reaction and to adjust the pH value to less than 4, and the mixture was dialyzed again. $H_2SO_4$ was added in a sufficient amount to give a concentration of 0.1N. Then the mixture was allowed to react for 1 hour at 80° C., dialyzed against distilled water and lyophilized. The powder thus obtained was dissolved in $CHCl_3$ and purified by Iatrobeads (a product of Iatron Co., Ltd.) column chromatography. Thus, approximately 100 mg of purified asailo $GM_2$ was obtained.

(3) Purification of fuco $GA_1$ 30 g of powder prepared by lyophilizing rat abdominal dropsy liver cancerous cells AH7974 F was extracted with 500 mg of a solvent mixture ($CHCl_3:CH_3OH:H_2O=10:5:1$). The extract was filtered and the residue was extracted with the same amount of a solvent mixture ($CHCl_3:CH_3OH=1:1$) and then with a solvent mixture ($CHCl_3:CH_3OH=1:2$). The extracts were combined and solvents were distilled off in vacuo. The residue was again dissolved in a solvent mixture ($CHCl_3:CH_3OH:H_2O=15:30:4$) and subjected to DEAE-Sephadex A-25 column chromatography to remove acidic lipids.

The neutral glycolipids fraction containing fuco $GA_1$ thus obtained was acetylated with a mixture of acetic anhydride and pyridine (2:3) and subjected to Florisil (an activated magnesium silicate) column chromatography to separate a glycolipid fraction from other phospholipids. Then the glycolipid fraction was deacetylated, dialyzed and lyophilized. The powder thus obtained was dissolved in $CHCl_3$ and purified by subjecting to Iatrobeads (a product of Iatron Co., Ltd.) column chromatography to obtain approximately 5 mg of purified fuco $GA_1$.

(4) Purification of paragloboside

Erythrocytic membrane was obtained by centrifuging 30 l of bovine blood to separate erythrocytes, hemolyzing the erythrocytes with 10 times as much 0.5% acetic acid solution and centrifuging at 8,000 rpm. The erythrocytic membrane was treated with 5 to 10 times as much acetone and dehydrated. Then it was extracted with successive, 20 times as much portions of $CHCl_3:CH_3OH$ (2:1), $CHCl_3:CH_3OH$ (1:1) and $CHCl_3:CH_3OH$ (1:2). The extracts were combined and concentrated in vacuo. The extract was dissolved in 2 liters of a solvent mixture ($CHCl_3:CH_3OH=2:1$) and mixed thoroughly with 500 ml of 0.9% NaCl. The upper layer was taken out, dialyzed and lyophilized. The powder thus obtained was subjected to Iatrobeads column chromatography to separate sialoylparagloboside composed of paragloboside conjugated with sialic acid. The obtained material was treated with 1N formic acid for 1 hour at 80° C. to deconjugate the sialic acid. Then the powder obtained by dialyzing and lyophilizing was dissolved in $CHCl_3$ and purified by Iatrobeads column chromatography to obtain approximately 50 mg of purified paragloboside.

2. Preparation of glycolipic antibody (1) Preparation of anti-asialo $GM_1$ anti-serum Two mg of asialo $GM_1$ and 4 mg of bovine serum albumin were suspended in 1 ml of distilled water. To the suspension, 1 ml of Freund's complete adjuvant was added to emulsify. Two ml portions of the emulsion was injected into a rabbit intracutaneously three times at two-week intervals. Two weeks after the final injection, whole blood was collected. Antibodies against asialo $GM_2$, fuco $GA_1$ and paragloboside might be prepared in the same manner as described above.

(2) Purification of anti-asialo $GM_1$ antibody 100 ml of the anti-asialo $GM_1$ anti-serum as prepared in Example 2(1) was salted out with a 50% saturated solution of ammonium sulfate. The precipitate was dissolved in 100 ml of a phosphate buffer solution (pH 7.2) and further salted out with a 20% saturated solution of ammonium sulfate to remove fibrinogen. The supernatent was salted out with a 35% saturated solution of ammonium sulfate to obtain a γ-globulin fraction. This fraction was dissolved in a small amount of a phosphate buffer solution (pH 7.2) and subjected to Sephadex G-200 column chromatography (2.5×110 cm). The obtained chromatogram indicated two peaks (small one is IgM fraction; the other is IgG fraction). The IgG fraction was dialyzed against distilled water and lyophilized.

50 mg of the IgG fraction thus obtained was dissolved in 30 ml of a phosphate buffer solution (pH 7.2) and poured into a column containing 10 ml of AH-Sepharose 4B conjugated with an oligosaccharide, the saccharide chain portion of asialo $GM_1$. Sepharose is a water soluble spherical form of an agarose gel. Then the column was washed with 120 ml of a phosphate buffer solution (pH 7.2) and eluted with 100 ml of 3.0M NaSCN. The elution was carried out at a rate of 10 ml/hour and 5 ml portions of fractions were collected.

The specific activity of the eluted anti-asialo $GM_1$ antibody was $2^5$ to $2^6$ complement-fixed titer/10 to 20 μg protein/ml.

The anti-asialo $GM_1$ antibody was desalted and concentrated by using a PM 30 Membrane (Amicon).

It was possible to use the AH-Sepharose 4B column conjugated with oligosaccharide of asialo $GM_1$ with washing with a phosphate buffer solution (pH 7.2) repeatedly until NaSCN was consumed.

100 mg of asialo $GM_1$ was dissolved in 20 ml of a mixture of methanol and hexane (4:3) and ozone was passed through the solution for 30 min. The suspended lipid-like materials were removed by centrifugation. An aqueous solution of sodium carbonate was added and the mixture was allowed to stand for 18 hours at room temperature (pH 10.5 to 11). Then it was centrifuged at 10,000 rpm for 20 min and Dowex 50 (H+ form) was added to the supernatant to remove sodium ions. Approximately 40 mg of oligosaccharide was obtained by purifying with Sephadex G-25 column chromatography.

Five mg of the obtained oligosaccharide and 20 mg of $NaBCNH_3$ were dissolved in 20 ml of distilled water. The resulting solution was mixed with 20 ml of AH- Sepharose 4B and refluxed for 5 hours. After cooling, the AH-Sepharose 4B reacted with oligosaccharide was centrifuged and washed with distilled water several times.

The AH-Sepharose 4B conjugated with oligosaccharide of asialo $GM_1$ thus obtained was equilibrated with a phosphate buffer solution (pH 7.2) and used to purify the antibody.

3. Preparation of anti-rabbit γ-globulin antibody

One mg of rabbit γ-globulin was dissolved in 2 ml of a physiological saline solution. Two ml of Freund's complete adjuvant was added to the solution to emulsify. The emulsion was injected into a goat intracutaneously five times at two-week intervals. Two weeks after the final injection, whole blood was collected to obtain anti-serum.

II. Assay of glycolipid by a competitive reaction

1. Assay of asialo $GM_1$

100 μl of standard asialo $GM_1$ or a serum sample, 100 μl of oligosaccharide/tyrosine/$^{125}I$ and 100 μl of anti-asialo $GM_1$ antibody were introduced into a test tube and incubated. Then 500 μl of anti-rabbit γ-globulin was introduced to the tube and further incubated.

After centrifuging at 3,000 rpm for 20 min, the supernatant was removed and the radioactivity of the precipitate was determined.

1-1 Preparation of the saccharide chain portion of asialo $GM_1$ 100 mg of asialo $GM_1$ was dissolved in 20 ml of a mixture of methanol and hexane (4:3). Then ozone was passed through the solution for 30 min. The suspended lipid-like materials were removed by centrifugation. An aqueous solution of sodium carbonate was added thereto and the mixture was allowed to stand for 18 hours at room temperature (pH 10.5 to 11). Then it was centrifuged at 10,000 rpm for 20 min and Dowex 50 ($H^+$ form) was added to the supernatant to remove sodium ions. Approximately 40 mg of oligosaccharide was obtained by purifying with Sephadex G-25 column chromatography.

1-2 Preparation of a tyrosine derivative of oligosaccharide of asialo $GM_1$

Five mg of the oligosaccharide of asialo $GM_1$ as prepared in II (b) and 20 mg of $NaBCNH_3$ were dissolved in 20 ml of distilled water. To this mixture, 5 mg of diaminohexane was added and refluxed for 5 hours. After cooling, the reaction liquor was concentrated in vacuo and subjected to Sephadex G-25 column chromatography to purify oligosaccharide conjugated hexylamine.

An N-hydroxysuccinimide ester was prepared from 10 mg of tyrosine in the presence of N-hydroxysuccinimide and dicyclohexylcarbodiimide. To this compound, 5 mg of oligosaccharide conjugated hexylamine prepared above was added and the mixture was allowed to react for 24 to 72 hours at room temperature. Approximately 6 mg of a tyrosine derivative of oligosaccharide of asialo $GM_1$ was obtained by purifying with Sephadex G-25 column chromatography.

1-3 $^{125}I$ labelling of oligosaccharide

20 μl of 1 mCi of $Na^{125}I$, 25 μl of a 0.5M phosphate buffer solution (pH 7.4), 1.5 μg of oligosaccharide of asialo $GM_1$ incorporating tyrosine and 25 μl of Chloramine T (1 mg/ml) were introduced into a test tube and allowed to react for 30 sec with shaking. Then 100 μl of sodium pyrosulfite (1 mg/ml) was added to stop the reaction.

Free $^{125}I$ was removed by Sephadex G-25 column chromatography to obtain oligosaccharide/tyrosine/$^{125}I$.

III Assay of glycolipid by a sandwich method

1. Assay of asialo $GM_1$

100 μl of standard asialo $GM_1$ or a serum sample and 100 μl of a 0.1M borate buffer solution (pH 8.6) were introduced into an assay plate. An anti-asialo $GM_1$ antibody bead was added to the mixture and incubated. Then the reaction liquor was removed and washed with a physiological saline solution twice. 200 μl of anti-asialo $GM_1$ antibody-$^{125}I$ was added thereto and incubated. After removing the reaction liquor and wasing with a physiological saline solution three times, the head was transferred to a counting tube to determine the radioactivity.

1-1 Preparation of solid-phase anti-asialo $GM_1$ antibody 500 polystyrene beads were introduced into a 100 ml bottle with a lid. Then 2 μg/bead of anti-asialo $GM_1$ antibody and 0.16 ml/bead of a 0.1M phosphate buffer solution (pH 7.8) was added thereto and the mixture was sealed and rotated overnight. Then it was washed with a 0.9% NaCl solution five times and dried to a desiccator to obtain a solid-phase antibody.

1-2 $^{125}I$ labelling of anti-asialo $GM_1$ antibody

20 μl of 1 mCi of $Na^{125}I$ and 25 μl of a 0.5M phosphate buffer solution (pH 7.5) were introduced into a test tube treated with silicone. Then 50 μl of an anti-asialo $GM_1$ antibody solution and 25 μl of Chloramine T (3 mg/ml) were added thereto. After thoroughly shaking for 20 to 30 sec to allow to react, 100 μl of sodium metabisulfite (3 mg/ml) was added to stop the reaction. To the reaction liquor 25 μl of potassium iodide (50 mg/ml) and 100 μl of a bovine serum alubumin solution (5%) were added. Free $^{125}I$ was removed by gel filtration with Sephadex G-25 to obtain $^{125}I$ labelled anti-asialo $GM_1$ antibody.

1-3 Fluorescein labelling of anti-asialo $GM_1$ antibody

Five mg of anti-asialo $GM_1$ antibody was dissolved in 1 ml of a 0.1M Tris-HCl buffer solution (pH 8.0). To this solution, an saline solution containing 50 μg of fluorescein isothiocyanate (FITC) was added with stirring. Then 1N NaOH was added slowly with stirring to adjust the pH to 9.5 and stirring was continued for additional 1 hour at room temperature to allow to react. After the completion of the reaction, the reaction liquor was dialyzed against a 0.01M phosphate buffer solution (pH 7.6) overnight at 4° C. and gel-filtered with Sephadex G-25 to obtain a labelled antibody.

1-4 Peroxidase labelling of anti-asialo $GM_1$ antibody

Five mg of peroxidase was dissolved in 1 ml of a 0.3M sodium hydrogencarbonate buffer solution (pH 8.1). After adding 0.1 ml of a 1% 1-fluoro-2,4-dinitrobenzene (FDNB) in ethanol solution, the mixture was allowed to react for 1 hour at room temperature. Then 1 ml of 0.06M sodium periodate was added and the mixture was allowed to react for 30 min at room temperature. Subsequently 1 ml of 0.16M ethylene glycol was added and the mixture was further allowed to react for 1 hour at room temperature. Then it was dialyzed against a 0.01M sodium carbonate buffer solution (pH 9.5) overnight at 4° C. Five mg of anti-asialo $GM_1$ antibody was added and the mixture was allowed to react for 2 hours at room temperature. Then 5 mg of sodium borohydride was added and the mixture was allowed to stand overnight at 4° C. Then it was dialyzed against a 0.01M phosphate-buffered sodium chloride solution overnight at 4° C. and gel-filtered with Sephadex G-200 to obtain a labelled antibody.

IV Assay of Glycolipid by an immunometric assay

1. Assay of asialo $GM_1$ by an immunometric assay with a radioisotope

100 μl of standard asialo $GM_1$ or a serum sample and 100 μl of a diluted solution of anti-asialo $GM_1$ antibody were introduced into an assay plate and incubated (the first reaction). Then a bead conjugated with asialo $GM_1$ was added to the mixture and further incubated (the second reaction). The bead was washed with 0.9% NaCl four times and incubated with 200 μl of anti-rabbit γ-globulin antibody-$^{125}$I (the third reaction). The bead was washed with 0.9% NaCl four times and transferred to a counting tube to determine the radioactivity.

An example of standard curve thus obtained and the results of assay of asialo $GM_1$ in blood of cancer patients are shown in FIGS. 1, 4, 5 and 6.

1-1 Preparation of insolubilized asialo $GM_1$ (immunoadsorbent)

Polystyrene beads were introduced in a beaker of an appropriate size to form one or two layers of the beads and washed with pure water five times. 0.2 ml/bead of an asialo $GM_1$ solution was added and the mixture was allowed to stand for 60 to 90 min at room temperature. After removing the asialo solution by decantation, the residue was washed with a phosphate-buffered sodium chloride solution (PBS) four times and stored in PBS at 4° C.

Insolubilized asialo $GM_2$, insolubilized fuco $GA_1$ and insolubilized paragloboside were prepared in the same manner as described above.

1-2 $^{125}$I labelling of anti-rabbit γ-globulin antibody

20 μl of 1 mCi of Na$^{125}$I and 25 μl of a 0.5M phosphate buffer solution (pH 7.5) were introduced into a test tube treated with silicone. Then 50 μl of an anti-rabbit γ-globulin antibody solution and 25 μl of Chloramine T (3 mg/ml) were added. After thoroughly shaking for 20 to 30 sec to allow to react, 100 μl of sodium metabisulfite (3 mg/ml) was added to stop the reaction. To the reaction mixture, 25 μl of potassium iodide (50 mg/ml) and 100 μl of a bovine serum albumin solution (5%) were added. Free $^{125}$I was removed by gel-filtration to obtain a $^{125}$I labelled anti-rabbit γ-globulin antibody.

2. Assay of asialo $GM_2$ by an immunometric assay with an enzyme

100 μl of standard asialo $GM_2$ and 100 μof a diluted solution of anti-asialo $GM_2$ antibody were introduced into an assay plate and incubated. Then a bead conjugated with asialo $GM_2$ was added and the mixture was further incubated. After washing the bead with a 0.01M phosphate-buffer sodium chloride solution (PBS) five times, 200 μl of peroxidase conjugated anti-rabbit γ-globulin antibody was added to the reaction mixture and incubated. After washing the bead with PBS five times, 225 μl of an enzyme substrate, which consisted of 0.05% hydrogen peroxide and 0.08% 5-aminosalicyclic acid (9:1) and was adjusted to pH 6.0 by NaOH, was added. After incubating the reaction mixture, the absorbance was determined at 450 nm.

Figure 1:
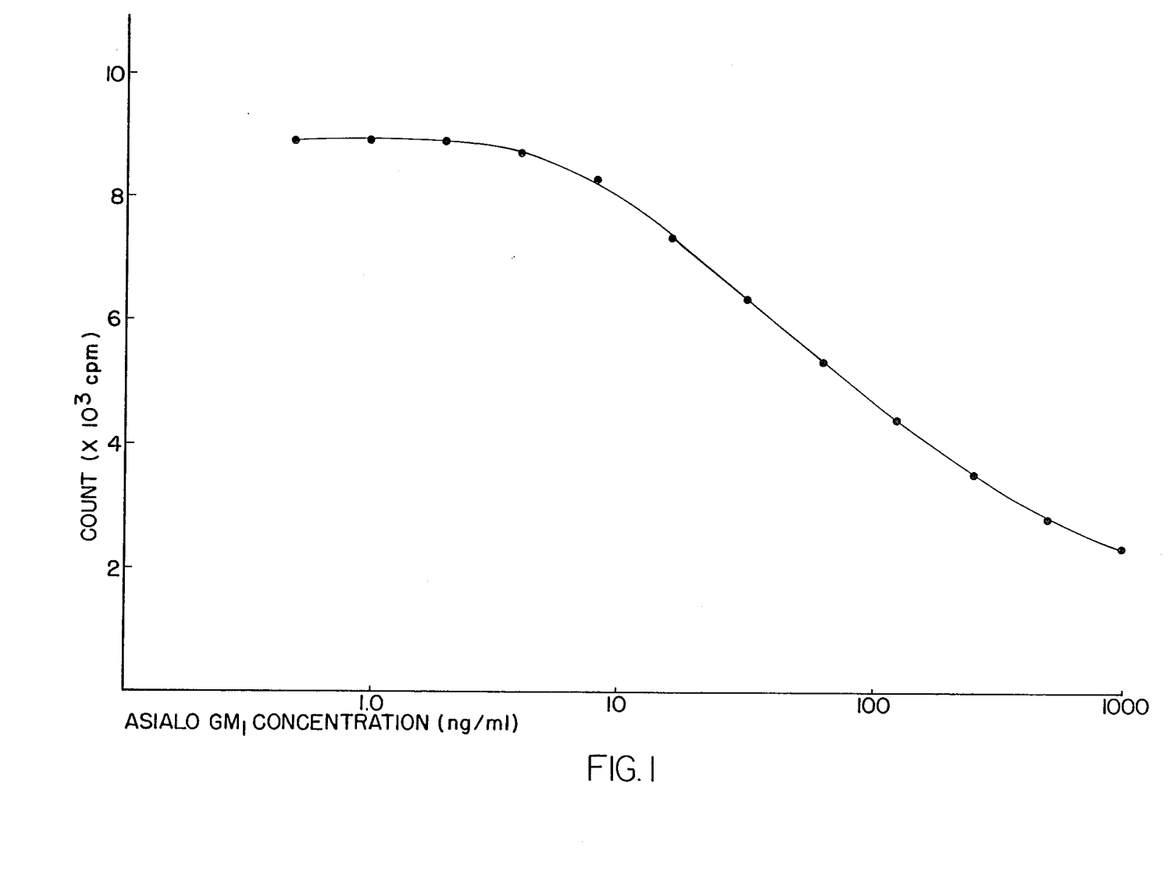
FIG. 1 is a standard curve obtained by an immunometric assay with a radioisotope by using standard asialo $GM_1$ solutions of known concentrations. In the figure, the abscissa refers to the asialo $GM_1$ concentration (ng/ml), while the ordinate refers to the count ($\times 10^3$ cpm). By using the standard curve, the asialo $GM_1$ concentration of a specimen can be determined by reading the concentration against the count thereof.
Figure 2:
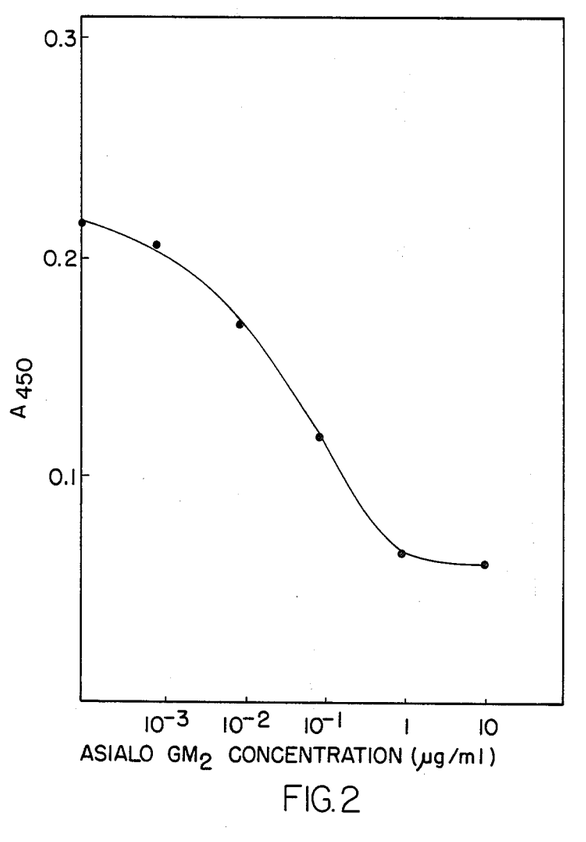
FIGS. 2 and 3 are standard curves of asialo $GM_2$ and paragloboside respectively, obtained by an immunometric assay using an enzyme.

An example of standard curves thus obtained is shown in FIG. 2.

2-1 Peroxidase labelling of anti-rabbit γ-globulin antiboy

Five mg of peroxidase was dissolved in 1 ml of a 0.3M sodium hydrogencarbonate buffer solution (pH 8.1). Then 0.1 ml of a 1% 1-fluoro-2,4-dinitrobenzene (FDNB) in ethanol solution was added to the solution and allowed to react for 1 hour at room temperature. Further 1 ml of 0.06M sodium periodate was added and the mixture was allowed to react for 30 min at room temperature. Subsequently 1 ml of 0.16M ethylene glycol was added and the mixture was allowed to react for 1 hour at room temperature. Then it was dialyzed against a 0.01M sodium carbonate buffer solution (pH 9.5) overnight at 4° C. After adding 5 mg of anti-rabbit γ-globulin antibody, the mixture was allowed to react for 2 hours at room temperature. Then 5 mg of sodium borohydride was added and the reaction mixture was allowed to stand overnight at 4° C. It was dialyzed against a 0.01M phosphate-buffered sodium chloride solution overnight at 4° C. and gel-filtered with Sephadex G-200 to obtain a labelled antibody.

3. Assay of paragloboside by an immunometric assay with an enzyme

100 μl of standard paragloboside and 100 μl of a diluted solution of anti-paragloboside antibody were introduced into an assay plate and incubated. Then a bead conjugated with paragloboside was added and the reaction mixture was further incubated. After washing the bead with a 0.01M phosphate-buffered sodium chloride solution (PBS) five times, 200 μl of peroxidase conjugated anti-rabbit γ-globulin antibody was added and incubated. After washing the bead with PBS five times, 225 μl of an enzyme substrate, which consisted of 0.05% hydrogen peroxide and 0.08% 5-aminosalicyclic acid (9:1) and wash adjusted to pH 6.0 by NaOH, was added. After incubating the reaction mixture, the absorbance was determined at 450 nm.

Figure 3:
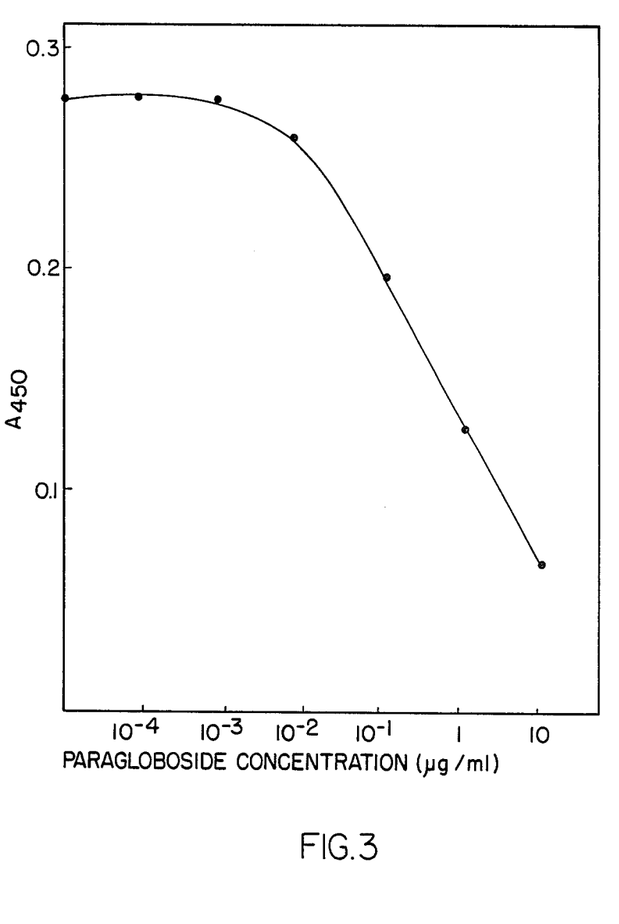

An example of standard curves thus obtained is shown in FIG. 3.

3-1 Peroxidase labelling of anti-rabbit γ-globulin antibody

Five mg of peroxidase was dissolved in a 0.3M sodium hydrogencarbonate buffer solution (pH 8.1). To this solution, 0.1 ml of a 1% 1-fluoro-2,4-dinitrobenzene (FDNB) in ethanol solution was added and allowed to react for 1 hour at room temperature. Then 1 ml of 0.06M sodium periodate was added and the mixture was allowed to react for 30 min at room temperature. Subsequently, 1 ml of 0.16M ethylene glycol was added and the mixture was allowed to react for 1 hour at room temperature. Then it was dialyzed against a 0.01M sodium carbonate buffer solution (pH 9.5) overnight at 4° C. After adding 5 mg of anti-rabbit γ-globulin antibody, the mixture was allowed to react for 2 hours at room temperature. Five mg of sodium borohydride was added and the reaction mixture was allowed to stand overnight at 4° C. Then it was dialyzed against a 0.01M phosphate-buffered sodium chloride solution overnight at 4° C. and gel-filtered with Sephadex G-200 to obtain a labelled antibody.

4. Fluorescein labelling of anti-rabbit γ-globulin antibody

Five mg of anti-rabbit γ-globulin antibody was dissolved in 1 ml of a 0.1M Tris-HCl buffer solution (pH 8.0). To this solution, a saline solution containing 50 μg of fluorescein isothiocyanate (FITC) was slowly added with stirring. Then 1N NaOH was slowly added to the solution with stirring to adjust the pH to 9.5 Stirring was continued for additional 1 hour to allow to react. After the completion of the reaction, the mixture was dialyzed against a 0.01M phosphate buffer solution (pH 7.6) overnight at 4° C. and gel-filtered with Sephadex G-25 to obtain a labelled antibody.

The obtained labelled antibody may be used as a labelled compound in an immunometric assay system.

What is claimed is:

1. A process for the detection of cancer which comprises:
   (a) competitively reacting a first glycolipid present in blood, thoracic cavity fluid, abdominal dropsy, or urine and a labelled second glycolipid, or labelled oligosaccharide, with an antibody specific to said first glycolipid, wherein said second glycolipid is the same as said first glycolipid and said oligosaccharide is a saccharide chain portion of said first glycolipid, and said first glycolipid being selected from the group consisting of
   (1) asialo $GM_1$: galactosyl-N-acetylgalactosaminyl-galactosyl-glucosyl-ceramide;
   (2) asialo $GM_2$: N-acetylgalactosaminyl-galactosyl-glucosyl-ceramide;
   (3) fuco $GA_1$: fucosyl-galactosyl-N-acetylgalactosaminyl-galactosyl-glucosyl-ceramide; and
   (4) paragloboside: galactosyl-N-acetylglucosaminyl-galactosyl-glucosyl-ceramide;
   (b) separating the labelled second glycolipid, or labelled oligosaccharide, having conjugated with said antibody, from the labelled second glycolipid, or labelled oligosaccharide, which has not conjugated with said antibody; and
   (c) determining the activity of at least one separated fraction.

2. The process as set forth in claim 1, wherein the second glycolipid, or oligosaccharide, is labelled with a labelling agent selected from the group consisting of a radioactive material, an enzyme and a fluorescent material.

3. The process as set forth in claim 1, wherein the oligosaccharide is a saccharide chain portion of a glycolipid selected from the group consisting of
   (1) asialo $GM_1$: galactosyl-N-acetylgalactosaminyl-galactosyl-glucosyl-ceramide;
   (2) asialo $GM_2$: N-acetylgalactosaminyl-galactosyl-glucosyl-ceramide;
   (3) fuco $GA_1$: fucosyl-galactosyl-N-acetylgalactosaminyl-galactosyl-glucosyl-ceramide; and
   (4) paragloboside: galactosyl-N-acetylglucosaminyl-galactosyl-glucosyl-ceramide.

4. A process for the detection of cancer which comprises:
   (a) reacting a glycolipid present in blood, thoracic cavity fluid, abdominal dropsy or urine with an insolubilized first anti-glycolipid antibody specific to said glycolipid to form a glycolipid/antibody conjugate, said glycolipid being selected from the group consisting of
   (1) asialo $GM_1$: galactosyl-N-acetylgalactosaminyl-galactosyl-glucosyl-ceramide;
   (2) asialo $GM_2$: N-acetylgalactosaminyl-galactosyl-glucosyl-ceramide;
   (3) fuco $GA_1$: fucosyl-galactosyl-N-acetylgalactosaminyl-galactosyl-glucosyl-ceramide; and
   (4) paragloboside: galactosyl-N-acetylglucosaminyl-galactosyl-glucosyl-ceramide;
   (b) reacting the glycolipid/antibody conjugate with a second anti-glycolipid antibody specific to said glycolipid, said second anti-glycolipid antibody carrying a labelling agent; and
   (c) determining the activity of said labelling agent on the glycolipid/antibody conjugate.

5. The process as set forth in claim 4, wherein the insolubilized first anti-glycolipid antibody is prepared by conjugating said first anti-glycolipid antibody with a solid phase.

6. The process as set forth in claim 4, wherein the labelling agent is selected from the group consisting of a radioactive material, an enzyme and a fluorescent material.

7. A process for the detection of cancer which comprises
   (a) reacting a glycolipid present in blood, thoracic cavity fluid, abdominal dropsy or urine with a given amount of an anti-glycolipid antibody specific to said glycolid, said anti-glycolipid antibody carrying a labelling agent, and said glycolipid being selected from the group consisting of
   (1) asialo $GM_1$: galactosyl-N-acetylgalactosaminyl-galactosyl-glucosyl-ceramide;
   (2) asialo $GM_2$: N-acetylgalactosaminyl-galactosyl-glucosyl-ceramide;
   (3) fuco $GA_1$: fucosyl-galactosyl-N-acetylgalactosaminyl-galactosyl-glucosyl-ceramide; and
   (4) paragloboside: galactosyl-N-acetylglucosaminyl-galactosyl-glucosyl-ceramide;
   (b) adsorbing unreacted anti-glycolipid antibody by an immunoadsorbent; and
   (c) determining the activity of said labelling agent on the immunoadsorbent.

8. The process as set forth in claim 7, wherein the immunoadsorbent is prepared by conjugating said glycolipid with an insoluble solid phase.

9. The process as set forth in claim 7, wherein the labelling agent is selected from the group consisting of a radioactive material, an enzyme and a fluorescent material.

10. A process for the detection of cancer which comprises:
    (a) reacting a glycolipid present in blood, thoracic cavity fluid, abdominal dropsy or urine with a given amount of an anti-glycolipid antibody specific to said glycolipid, said glycolipid being selected from the group consisting of
    (1) asialo $GM_1$: galactosyl-N-acetylgalactosaminyl-galactosyl-glucosyl-ceramide;
    (2) asialo $GM_2$: N-acetylgalactosaminyl-galactosyl-glucosyl-ceramide;
    (3) fuco $GA_1$: fucosyl-galactosyl-N-acetylgalactosaminyl-galactosyl-glucosyl-ceramide; and
    (4) paragloboside: galactosyl-N-acetylglucosaminyl-galactosyl-glucosyl-ceramide;
    (b) absorbing unreacted anti-glycolipid antibody by an immunoadsorbent;
    (c) reacting said anti-glycolipid antibody adsorbed on the immunoadsorbent with an anti-IgG antibody specific to said anti-glycolipid antibody, said anti-IgG antibody carrying a labelling agent; and
    (d) determining the activity of the labelling agent conjugated with the immunoadsorbent.

11. The process as set forth in claim 10, wherein the immunoadsorbent is prepared by conjugating said glycolipid with an insoluble phase.

12. The process as set forth in claim 10, wherein the labelling agent is selected from the group consisting of a radioactive material, an enzyme and a fluorescent material.

13. A process for the detection of cancer which comprises reacting, in vitro, a glycolipid present in blood, thoracic cavity fluid, abdominal dropsy or urine with an antibody specific to said glycolipid, said glycolipid being selected from the group consisting of (1) asialo $GM_1$: galactosyl-N-acetylgalactosaminyl-galactosyl-glucosyl-ceramide;
(2) asialo $GM_2$: N-acetylgalactosaminyl-galactosyl-glucosyl-ceramide;
(3) fuco $GA_1$: fucosyl-galactosyl-N-acetylgalactosaminyl-galactosyl-glucosyl-ceramide; and
(4) paragloboside: galactosyl-N-acetylglucosaminyl-galactosyl-glucosyl-ceramide.

* * * * *

UNITED STATES PATENT AND TRADEMARK OFFICE
CERTIFICATE OF CORRECTION

PATENT NO. : 4,757,003
DATED : July 12, 1988
INVENTOR(S) : Makoto Matsumoto, et al.

It is certified that error appears in the above-identified patent and that said Letters Patent is hereby corrected as shown below:

Column 4, line 6: "detecting" should read as --detection--

Column 6, line 7: "glycolipic" should read as --glycolipid--

Column 8, lines 4-5: "$^{1-2}5I.$" should read as --$^{125}I.$--

Column 8, line 16: "wasing" should read as --washing--

Column 8, line 18: "head" should read as --bead--

Column 8, line 27: "to" should read as --in--

Column 9, line 20: "curve" should read as --curves--

UNITED STATES PATENT AND TRADEMARK OFFICE
CERTIFICATE OF CORRECTION

PATENT NO. : 4,757,003
DATED : July 12, 1988
INVENTOR(S) : Makoto Matsumoto, et al.

It is certified that error appears in the above-identified patent and that said Letters Patent is hereby corrected as shown below:

Column 9, line 53: "µof" should read as --µℓ of--

Column 9, line 58: "buffer" should read as --buffered--

Column 10, line 35: "wash" should read as --was--

Column 12, line 56, Claim 10: "absorbing" should read as --adsorbing--

Signed and Sealed this

Thirteenth Day of March, 1990

Attest:

JEFFREY M. SAMUELS

*Attesting Officer*   *Acting Commissioner of Patents and Trademarks*